United States Patent [19]

Goldberg

[11] 4,290,944

[45] Sep. 22, 1981

[54] ANTIGENIC PEPTIDE COMPOUND

[75] Inventor: Erwin Goldberg, Evanston, Ill.

[73] Assignee: Northwestern University, Evanston, Ill.

[21] Appl. No.: 174,011

[22] Filed: Jul. 31, 1980

[51] Int. Cl.³ .......................................... C07C 103/52
[52] U.S. Cl. ............................................. 260/112.5 R
[58] Field of Search ................................. 260/112.5 R

[56] References Cited

U.S. PATENT DOCUMENTS 4,016,259  4/1977  Kent, Jr. ...................... 260/112.5 R
4,161,522  7/1979  Hamburger ................... 260/112.5 R

OTHER PUBLICATIONS

T. E. Wheat, et al., Biochem. & Biophys. Res. Commun. 74, 1977 1066–1070.
Goldberg, J. of Biological Chem. 247, 1972 2044–2048.

*Primary Examiner*—Delbert R. Phillips

[57] ABSTRACT

The novel antigenic peptide compound of this invention comprises a sequence of seven amino acids, namely, methionine-glutamine-lysine-aspartic acid-leucine-glutamic acid-leucine, all of the amino acids being in their L-forms. The compound has utility in vaccines for reducing the fertility of mammals.

1 Claim, No Drawings

ANTIGENIC PEPTIDE COMPOUND

BACKGROUND AND PRIOR ART

Mammalian spermatozoa have been known to be antigenic for many years. More recently, it has been demonstrated that mammalian sperm contain an antigenic enzyme, which is known as the C4 isozyme of lactate dehydrogenase (LDH-X, LDH-$C_4$). LDH-$C_4$ has been isolated in pure crystalline form from mouse testes. Goldberg (1972) *J. Biol. Chem.* 247:2044-2048. The enzyme has a molecular weight of 140,000 and is composed of four identical C subunits. The amino acid sequence and three-dimensional structure of LDH-$C_4$ has been studied and partially determined by a number of investigators. See Musick et al (1976) *J. Mol. Biol.* 104:659-668; and Wheat et al (1977) *Biochem. & Biophys. Res. Comm.*, 74, No. 3:1066-1077. Wheat et al determined the sequence of the essential thiol peptide from amino acid 159 to 171, and found this to be nearly identical to essential thiol peptides from other vertebrate LDH isozymes.

In 1974, Dr. Erwin Goldberg reviewed the effects of immunization with LDH-X (LDH-$C_4$) on fertility, and advanced the possibility that "by using a defined macromolecular constituent of sperm it becomes possible to elucidate its primary structure in terms of amino acid sequence, to map specifically the antigenic determinant(s) responsible for inducing infertility, and then to construct synthetic peptides containing these determinants. Possessing the capability for synthesizing a molecule with such properties, makes the immunological approach to fertility control feasible." Karolinska Symposia on Research Methods in Reproductive Endocrinology, 7th Symposia: Immunological Approaches to Fertility Control, Geneva, 1974 202-222. However, such synthetic antigenic peptides remained a goal and not an achievement, although their theoretical desirability had been recognized. In 1979, Dr. Erwin Goldberg summarized the state of the art as follows:

"In conclusion, and on a practical basis immunotherapy for birth control requires more than effectiveness, specificity, reversibility, and absence of systemic side reaction. Rather large amounts of the antigen must be available in unequivocally pure form. This condition probably cannot be met by a natural product enzyme antigen from sperm or testes. Rather, contraceptive technology requires a synthesizable peptide fragment retaining antigenicity and provoking a response which impairs fertility. Completion of the structural analysis of LDH-$C_4$ should allow mapping of antigenic determinants and synthesis of such peptides for use in a new contraceptive technology," *Recent Advances in Reproduction and Regulation of Fertility*, G. P. Talwar, editor, Elsevier/North Holland Biomedical Press (1979).

SUMMARY OF INVENTION

It has now been discovered that an antigenic peptide can be prepared by synthesizing a linear sequence of seven amino acids comprising: methionine-glutamine-lysine-aspartic acid-leucine-glutamic acid-leucine. All of the amino acids used to prepare the foregoing peptide are in their L-form. The N-terminal is methionine and the C-terminal is leucine. Although not known with certainty, it is believed that the foregoing sequence of seven amino acids corresponds to amino acids 325 to 332 of LDH-$C_4$. This is contrary to a recently published tentative sequence. See Musick et al (1979) *J. Biol. Chem.*, 254, No. 16:7621-7623.

DESCRIPTION OF INVENTION

The present invention relates to a novel antigenic linear peptide having a chain length of seven amino acids. The formula of this peptide can be represented as follows:

In the foregoing formula, the letter "N" designates the N-terminal amino acid, while the letter "C" designates the C-terminal amino acid. Met, Gln, Lys, Asp, Glu, and Leu represent the L-amino acid forms, respectively, of methionine, glutamine, lysine, aspartic acid, glutamic acid, and leucine.

The peptide compound of the present invention can be synthesized from its constituent amino acids. For example, the synthesis can be carried out by the Merrifield solid phase method, as described in *J.A.C.S.* 85:2149-2154 (1963). This solid phase method for synthesizing sequences of amino acids is also described in Stewart and Young, *Solid Phase Peptide Synthesis* (W. H. Freeman and Co., San Francisco, 1969), pages 1-4. In this procedure, the C-terminal amino acid, such as leucine for the compound of this invention, is attached to chloromethylated polystyrene-divinylbenzene copolymer beads. Each subsequent amino acid, with suitable protecting group, is then added sequentially to the growing chain. For example, as described in the Merrifield article, the protective group may be a carbobenzoxy group. By the procedure of coupling, deprotection, and coupling of the next amino acid, the desired amino acid sequence and chain length can be produced. As a final step, the protective group is removed from the N-terminal amino acid (viz. methionine), and the C-terminal amino acid is cleaved from the resin, using a suitable reagent, such as trifluoroacetic acid and hydrogen bromide. Since this synthesis procedure is well known, it is not believed that it will be necessary to further describe it herein. The peptide of this invention can be prepared by this synthesis procedure for use in reducing the fertility of mammals.

To utilize the antigenic peptide of this invention in the form of a fertility reducing vaccine, the peptide is conjugated to a carrier molecule, which is preferably a protein which itself elicits an antigenic response and which can be safely administered. For example, the peptide can be coupled to tetanus toxoid for administration by intramuscular injection. For example, a mixture of 1 μMole tetanus toxoid, 60 μMoles antigenic peptide, and 18 millimoles 1-ethyl-3-(3dimethyl aminopropyl) carbodiimide hydrochloride reacted in water (pH 6) for 12 hours at room temperature and 24 hours at 4° gives a product containing 3.5 moles of peptide/mole tetanus toxoid. Excess reactants can be removed by dialysis or gel filtration. See Pique et al, *Immunochemistry*, 15:55-60 (1978). Alternatively, the peptide may be coupled using bisdiazotized benzidine [Bassiri et al, *Endocrinology*, 90:722 (1972)] or glutaraldehyde.

For intramuscular injection, the coupled peptide may be suspended in a sterile isotonic saline solution, or other conventional vehicle, and, if desired, an adjuvant may be included. A preferred use of such a vaccine is for administration to human females. Antibodies will be formed, which will appear in the oviduct fluids and thereby achieve a significant reduction in fertility. For this purpose, the amount to be administered will range from about 1 to 10 milligrams (mg) of the antigenic peptide.

I claim:
1. The antigenic linear peptide compound having the formula: N-Met-Gln-Lys-Asp-Leu-Glu-Leu-C wherein N-Met is N-terminal L-methionine, Leu-C is C-terminal L-leucine, and Gln, Lys, Asp, Glu, and Leu are the L-amino acid forms, respectively, of glutamine, lysine, aspartic acid, glutamic acid, and leucine.

* * * * *

UNITED STATES PATENT AND TRADEMARK OFFICE
CERTIFICATE OF CORRECTION

PATENT NO. : 4,290,944
DATED : September 22, 1981
INVENTOR(S) : Erwin Goldberg

It is certified that error appears in the above-identified patent and that said Letters Patent are hereby corrected as shown below:

In column 1 of the patent following the title insert the following notice: -This invention was developed in part under Grant HD 05863 by The National Institutes of Health.-

Signed and Sealed this

Fifth Day of June 1984

[SEAL]

Attest:

Attesting Officer

GERALD J. MOSSINGHOFF

*Commissioner of Patents and Trademarks*